United States Patent
Spaulding et al.

(10) Patent No.: US 6,727,072 B2
(45) Date of Patent: Apr. 27, 2004

(54) EGF-R DETECTION KIT

(75) Inventors: Elizabeth O. Spaulding, Santa Barbara, CA (US); Marc E. Key, Ojai, CA (US)

(73) Assignee: Dako Corporation, Carpinteria, CA (US)

(*) Notice: Subject to any disclaimer, the term of this patent is extended or adjusted under 35 U.S.C. 154(b) by 451 days.

(21) Appl. No.: 09/846,551

(22) Filed: May 1, 2001

(65) Prior Publication Data

US 2002/0164660 A1 Nov. 7, 2002

(51) Int. Cl.$^7$ ................................. G01N 33/53
(52) U.S. Cl. .................... 435/7.21; 435/7.1; 435/387.7; 435/250; 435/23; 435/960; 435/975; 436/501; 436/507; 436/810; 436/822; 436/808; 436/813; 514/2
(58) Field of Search .................. 436/501, 822, 436/507, 810, 808, 813; 435/7.1, 7.23, 387.7, 250, 23, 960, 975; 514/2

(56) References Cited

U.S. PATENT DOCUMENTS

| | | | |
|---|---|---|---|
| 5,344,760 A | * | 9/1994 | Harvey et al. ............... 435/7.5 |
| 5,459,061 A | * | 10/1995 | Sato et al. ................... 435/334 |
| 5,674,753 A | * | 10/1997 | Harvey et al. ............... 436/501 |
| 6,235,729 B1 | * | 5/2001 | Chen et al. ................. 514/176 |

OTHER PUBLICATIONS

Rodeck et al., Cancer Research. 47:3692–3696. 1987.*
Sato et al., Mol. Biol. Med. 1:511–529. 1983.*
Takahashi et al., Cancer Research. 47:3847–3850. 1987.*
Fendly et al., Cancer Research. 50:1550–1558, 1990.*
Gill et al., The Journal of Biol. chem. 259(12):7755–7760. 1984.*
Key, Marc. The J. of Histotechnology. 25(4):243–245. 2002.*
Masui et al., Cancer Research. 46:5592–5598. 1986.*

* cited by examiner

Primary Examiner—Bao-Thuy L. Nguyen
(74) Attorney, Agent, or Firm—Michael G. Petit

(57) ABSTRACT

A kit containing the reagents necessary for the qualitative or quantitative demonstration of epidermal growth factor receptor (EGFR) in formalin-fixed, paraffin-embedded tissue sections. A immunohistochemical staining procedure is employed which utilizes a primary monoclonal mouse antibody that selectively binds to EGFR. The primary antibodies bound to tissue antigens are detected using a peroxidase labeled polymer that is conjugated with secondary anti-mouse immunoglobulin antibodies. The enzymatic conversion of the subsequently applied chromogen results in formation of a visible reaction product at the site of the EGFR antigen. Following development of the chromogen, specimens may then be counterstained and coverslipped. Results are interpreted using a light microscope or other optical imaging device. The detection system is adapted for both manual and automated staining.

13 Claims, 1 Drawing Sheet

Control Slides: Control slides each contains three pelleted, formalin-fixed, paraffin-embedded cell lines, which represent different amounts of the EGFR protein expression. The immunohistochemical staining scores of the three cell pellets are 1+, 2+ and 3+.

Cell Line    Expression level
A: _____   _____
B: _____   _____
C: _____   _____

Control Slides: Control slides each contains three pelleted, formalin-fixed, paraffin-embedded cell lines, which represent different amounts of the EGFR protein expression. The immunohistochemical staining scores of the three cell pellets are 1+, 2+ and 3+.

```
     Cell Line    Expression level
A:   _____    _____
B:   _____    _____
C:   _____    _____
```

EGF-R DETECTION KIT

BACKGROUND OF THE INVENTION

1. Field of the Invention

A kit and method for using the kit for the qualitative demonstration or quantitative determination of epidermal growth factor receptor (EGFR) in formalin-fixed, paraffin-embedded tissue sections.

2. Prior Art

Growth factors are substances that induce cell proliferation, typically by binding to specific receptors on cell surfaces. One such growth factor is epidermal growth factor (EGF). EGF induces proliferation of a variety of cells in vivo, and is required for the growth of most cultured cells. The EGF receptor is a 170–180 kD membrane-spanning glycoprotein, which is detectable on a wide variety of cell types. The extracellular N-terminal domain of the receptor is highly glycosylated and binds EGF antibodies that selectively bind to epidermal growth factor receptor (EGFR). Agents that competitively bind to EGFR have been used to treat certain types of cancer. Sato et al., in U.S. Pat. No. 5,459,061, discloses the structure of a immunogenic segment of the EGFR protein that is presented on the cell surface. The inventors disclose a specific monoclonal antibody (Mab) produced by a hybridoma cell line which competes with EGF to bind to the segment of EGFR. Sato et al. discuss an ELISA competitive binding assay useful for the in vitro testing of three anti-EGFR Mab's for their ability to inhibit the growth of a human cancer cell line. Sato et al. do not suggest or otherwise extend the application of the in vitro test of live cancer cell lines to the detection of EGFR in formalin-fixed specimen tissue.

Herlyn et al., in U.S. Pat. No. 5,470,571, disclose the use of radio labeled Mab 425 for treating gliomas that express EGF receptor. Herlyn et al. report that anti-EGFR antibodies may either stimulate or inhibit cancer cell growth and proliferation. Unfortunately, the inventors do not discuss a need for a test for examining suspect tissue for the presence of EGFR that would be predictive of the result (i.e., stimulation, inhibition or no effect) to be expected by administering any particular Mab.

Holzer et al., in U.S. Pat. No. 5,824,782, disclose the use of immunoconjugates, more specifically, anti-EGFR Mab's or fragments thereof conjugated to a chemokine such as IL-8, the fusion protein binding to EGFR and exhibiting cytotoxic and/or chemotactic activity. Holzer et al. demonstrates the binding properties of their immunoconjugates by coating a substrate with EGFR, incubating the coated substrate with immunoconjugate then exposing the coated substrate to a monoclonal antibody bound to peroxidase. A chromogenic peroxidase substrate was added and the presence of the immunoconjugate on the substrate being determined photometrically. The test employs free EGFR coated on a substrate and is not suitable for examining tissue sections comprising biopsy material from a patient. They do not suggest using such a test for examining a tissue sample or for predicting the efficacy of anti-EGFR Mab's for treating a particular tumor. Similarly, Wels et al., in U.S. Pat. No. 5,942,602, disclose a variety of compounds exhibiting specific binding to EGFR and disclose a method for imaging EGFR expressing cells. There is no disclosure of the use of anti-EGFR Mab's for detecting EGFR in tissue samples as a method for selecting patients that will be responsive to anti-EGFR therapy or for predicting the therapeutic efficacy of any particular Mab-based therapy for cancer patients.

Other monoclonal antibodies having specificity for EGFR, either alone or conjugated to a cytotoxic compound, have been reported as being effective for treating certain types of cancer. Bendig et al, in U.S. Pat. No. 5,558,864, disclose therapeutic anti-EGFR Mab's for competitively binding to EGFR. Heimbrook et al., in U.S. Pat. No. 5,690,928, disclose the use of EGF fused to a Pseudomonas species-derived endotoxin for the treatment of bladder cancer. Brown et al., in U.S. Pat. No. 5,859,018, disclose a method for treating diseases characterized by cellular hyperproliferation mediated by, inter alia, EGF.

Many tumors of mesodermal and ectodermal origin overexpress the EGF receptor. For example, the EGF receptor has been shown to be overexpressed in many gliomas, squamous cell carcinomas, breast carcinomas, melanomas, invasive bladder carcinomas and esophageal cancers. In addition, studies with primary human mammary tumors have shown a correlation between high EGF receptor expression and the presence of metastases, higher rates of proliferation, and shorter patient survival.

As mentioned above, attempts to exploit the EGF receptor system for anti-tumor therapy have generally involved the use of monoclonal antibodies against the EGF receptor. Magnani et al., in U.S. Pat. No. 6,008,203 disclose carbohydrates and carbohydrate analogs that bind to epidermal growth factor receptors. Methods of using such carbohydrates or analogs for a variety of uses related to the EGF receptor are also discussed. Methods for killing or inhibiting the growth of tumor cells with increased EGF receptor activity are disclosed. The preferred compositions comprise a sialylated lactose carbohydrate. The composition reportedly inhibits EGFR kinase activity thereby inhibiting the growth of EGFr-associated tumor cells.

Notwithstanding the reported therapeutic utility of compounds targeting EGFR for certain types of cancer, there have been relatively few assays developed for tumor-related EGFR expression in actual cancer patients. In U.S. Pat. No. 5,710,010, the contents of which are incorporated herein by reference thereto, Vogelstein et al disclose anti-mutated EGFR Mab's for identifying cells expressing mutated EGFR and for diagnosing medical conditions associated therewith. In addition, they present the cDNA sequence of normal EGFR and mutated segments of the gene. It appears that both the overexpression of EGFR and the expression of mutated EGFR are characteristic of some tumors and may be used as markers for targeted therapies. There is, therefore, a need for a kit and method for determining the presence of EGFR on cancerous tissue removed from a patient as, for example, by biopsy, in order to evaluate the appropriateness of an in vivo therapy employing EGFR-targeting cytotoxic agents.

SUMMARY

It is a primary object of the present invention to provide a kit, and a method for using the kit, operable for determining the presence of EGFR in tissue sections.

It is a further object of the invention to provide a kit, and a method for using the kit, operable for determining the presence of EGFR in tissue sections comprising tissue embedded in paraffin.

It is a yet a further object of the invention to provide a kit, and a method for using the kit, operable for determining the presence of EGFR in tissue sections that can be performed with minimal training and without expensive specialized equipment.

It is a yet a further object of the invention to provide a kit, and a method for using the kit, for selecting certain patients from a population of cancer patients wherein the selected patients have tumors that express EGFR and are most likely to respond to anti-EGFR therapy.

In accordance with the above objectives of the invention, there is provided a kit containing the reagents necessary for the qualitative demonstration of epidermal growth factor receptor (EGFR) in formalin-fixed, paraffin-embedded tissue sections. A two-step immunohistochemical staining procedure is employed which utilizes a monoclonal mouse antibody to EGFR. The anti-EGFR antibodies, which are bound to tissue antigens by incubation therewith, are detected using a peroxidase labeled polymer that is conjugated with secondary anti-mouse antibody antibodies. The enzymatic conversion of the subsequently applied chromogen, preferably DAB, results in formation of a visible reaction product at the site of the EGFR antigen. Following development of the chromogen, specimens may then be counterstained and coverslipped. Results are interpreted using a light microscope. This detection system should be applicable for both manual and automated staining.

The features of the invention believed to be novel are set forth with particularity in the appended claims. However the invention itself, both as to organization and method of operation, together with further objects and advantages thereof may be best be understood by reference to the following description taken in conjunction with the accompanying drawings in which:

DESCRIPTION OF THE PREFERRED EMBODIMENTS

Figure 1:
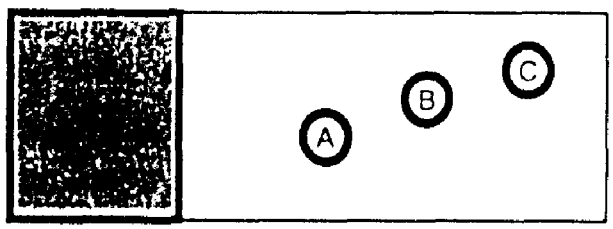
FIG. 1 is an example of a control slide adapted to be used for the qualitative detection of EGFR using the kit and method of the present invention.

The present invention provides a kit and a method for using the kit for detecting EGFR in tissue that has been embedded in a paraffin block or similar embedding material prior to the time the kit is used. Thus, the selection of reagents and certain of the steps disclosed herein assume that the tissue being analyzed is sectioned from tissue embedded in a paraffin block and wherein the sectioned tissue has been affixed to a slide. With this in mind, a preferred embodiment of the invention includes the following reagents:

| Reagent No. | Quantity | Description |
| --- | --- | --- |
| 1 | 110 mL | Proteinase K: Ready to use Proteinase K proteolytic enzyme diluted in 0.05 M Tris-HCl, 0.015M sodium azide, pH 7.5. |
| 2 | 110 mL | Peroxidase Block: 0.03% hydrogen peroxide containing sodium azide. |
| 3 | 1 mL | Monoclonal Mouse Anti-human EGFR, Clone 2-18C9: Monoclonal antibody supplied in concentrated form at 581 µg/mL as tissue culture supernatant (containing fetal calf serum) dialyzed against 0.05M Tris-HCl, pH 7.2, and 0.015M sodium azide. |
| 4 | 1 mL | Mouse IgG$_1$ Isotype Control: Monoclonal mouse IgG$_1$ antibody provided in concentrated form at 100 µg/mL as tissue culture supernatant (containing fetal calf serum) dialyzed against 0.05M Tris-HCl. pH 7.2, and 0.015M sodium azide. |
| 5 | 110 mL | Primary Antibody Diluent: Tris-based antibody diluent comprised of 0.05M Tris-HCl pH 7.6 containing stabilizing protein and 0.015M sodium azide. |
| 6 | 110 mL | Visualization Reagent: Peroxidase labeled polymer conjugated to affinity-isolated goat anti-mouse immunoglobulins in Tris-HCl buffer containing stabilizing protein and an antimicrobial agent. |

-continued

| Reagent No. | Quantity | Description |
| --- | --- | --- |
| 7 | 120 mL | DAB Substrate Buffer: Imidazole-HCl buffer pH 7.5, containing hydrogen peroxide, stabilizers, enhancers and an antimicrobial agent. |
| 8 | 5 mL | DAB Chromogen: 3,3'-diaminobenzidine in chromogen solution. |
| 9 | 12 packets | TBS (Tris Biffered Saline): Packets of TBS containing Tris base, Tris-HCl and NaCl. Each packet makes 5 liters of 50mM Tris-HCl, 150mM NaCl Tris-Buffered Saline, pH 7.6. |
| 10 | 100 mL | Tween 20 |
|  |  | 30 Control Slides: Control slides, indicated at numeral 10 in FIG. 1, each contain three pelleted, formalin-fixed, paraffin-embedded cell lines, which represent different amounts of the EFGR protein expression. |

Reagent Preparation

It is convenient to prepare the following reagents prior to staining. Distilled water may be used for rinsing the Proteinase K, Peroxidase Block, DAB Substrate-Chromogen and counterstain.
Wash Buffer:
   Add 5 L (5000 mL) of deionized water to a 5 L carboy, flask or beaker. Empty contents of one packet of TBS (Reagent 9) and use a magnetic stir plate to dissolve the TBS granules. Add 2.5 mL of Tween 20 (Reagent 10) to the Tris-buffered saline solution and mix. TBS solution should be stored at 2–8° C. to inhibit bacterial growth. TBS solution should be discarded if it becomes turbid. If stored at 4° C., the expected shelf life 7 days. If stored at room temperature, the expected shelf life is 4 days.
Primary Antibody and Negative Control Reagent:
   Dilute primary antibody (Reagent 3) and negative control reagent (Reagent 4) to optimal concentration of 5.81 ug/mL in primary antibody diluent (Reagent 5).
Substrate-Chromogen Solution:
   Add one drop (or 20 µl) of the DAB Chromogen (Reagent 8) per 1 mL of DAB Substrate Buffer (Reagent 7) and mix well. Each 1 mL is sufficient for ten tissue sections. Prepared Substrate-Chromogen is stable for 14 days if stored at 2–8° C.
Counterstain:
   An aqueous-based counterstain such as Mayer's hematoxylin (DAKO® Code No. S3309) is recommended. Follow counterstaining by hematoxylin with a thorough rinse in distilled water, and then immerse tissue slides into a bath of 37 mM ammonia (see Step 7) or similar bluing agent. Thirty-seven mM ammonia water is prepared by mixing 2.5 mL of 15M (concentrated) ammonium hydroxide with 1 liter of water.
   Unused 37 mM ammonia may be stored at room temperature (20–25° C.) in a tightly capped bottle for up to 12 months.
Mounting Media:
   Mounting media such as DAKO® Faramount Aqueous Mounting Medium, Ready-to-use (Code No. S3025) or DAKO Glycergel® Mounting Medium (Code No. C0563) is recommended for aqueous mounting. Liquify DAKO Glycergel® by warming to approximately 40° C.±5° C. prior to use. Non-aqueous, permanent mounting is also suitable such as DAKO® Ultramount (Code No. S1964).
Specimen Collection and Preparation
   Tissues preserved in neutral buffered formalin for routine processing and paraffin embedding, are suitable for use. Biopsy specimens should be cut into blocks of approximately 1.0×1.0×0.5 cm and immediately placed into 5–10 mL of neutral buffered formalin per block. Tissue should be fixed in formalin for 18–24 hours. After fixation, processing may be completed using an automatic tissue processor. Tissues are dehydrated using graded alcohols, cleared with xylene or xylene substitute, and infiltrated with paraffin wax. To minimize denaturing of antigens, temperatures greater than 60° C. must be avoided during processing.

Tissue blocks may be stored or sectioned on completion of embedding. Properly fixed and embedded tissues expressing the EGFR protein will keep indefinitely prior to sectioning and slide mounting if stored in a cool place (15–25° C.).

Staining Procedure

Deparaffinization and Rehydration:

Prior to staining, specimens must be deparaffinized to remove embedding media and rehydrated. Avoid incomplete removal of paraffin since residual medium can cause an increase in background and obscure specific staining.

1. Place slides in a xylene or xylene substitute bath and incubate for 5 (±1) minutes. Change baths and repeat once.
2. Tap off excess liquid and place slides in absolute ethanol for 3 (±1) minutes. Change baths and repeat once.
3. Tap off excess liquid and place slides in 95% ethanol for 3 (±1) minutes. Change baths and repeat once.
4. Tap off excess liquid and place slides in distilled or deionized water for a minimum of 30 seconds.

Step 1 Proteinase K Treatment

Tap off excess buffer and wipe around specimen.

Apply enough Proteinase K to cover specimen.

Incubate 10 (±1) minutes.

Rinse gently with distilled water or buffer solution from a wash bottle and place in a fresh buffer bath.

Step 2 Peroxidase Block

Tap off excess buffer and wipe around specimens.

Apply enough Peroxidase Block to cover specimen.

Incubate 5 (±1) minutes.

Rinse gently with distilled water or buffer solution from a wash bottle and place in a fresh buffer bath.

Step 3 Primary Antibody or Negative Control Reagent

Tap off excess buffer and wipe around specimens.

Apply enough diluted primary antibody or negative control reagent to cover specimen.

Incubate 30 (±1) minutes.

Rinse gently with buffer solution from a wash bottle and place in a fresh buffer bath.

Step 4 Visualization Reagent

Tap off excess buffer and wipe around specimens.

Apply enough visualization reagent to cover specimen.

Incubate 30 (±1) minutes.

Rinse gently with buffer solution from a wash bottle and place in a fresh buffer bath.

Step 5 Substrate-Chromogen

Tap off excess buffer and wipe around specimens.

Apply enough prepared DAB Substrate-Chromogen to cover specimen.

Incubate 10 (±1) minutes.

Rinse gently with distilled water from a wash bottle and place in a fresh buffer bath.

The kit and method described hereinabove is particularly useful for identifying patients having tumors that are likely to respond to anti-EGFR therapy. While particular embodiments of the present invention have been illustrated and described, it would be obvious to those skilled in the art that various other changes and modifications can be made without departing from the spirit and scope of the invention. For example, the procedure described herein can also be adapted for use with automated staining instruments. It is therefore intended to cover in the appended claims all such changes and modifications that are within the scope of this invention.

What we claim is:

1. A kit operable for detecting the presence of epidermal growth factor receptor in cells comprising a tissue, the kit comprising:

(a) a proteolytic enzyme comprising Proteinase K diluted in 0.05M Tris-HCl, 0.015M sodium azid, pH 7.5;

(b) a peroxidase;

(c) Monoclonal Anti-human EGFR antibody derived from a nonhuman source (d) $IgG_1$ Isotype Control comprising monoclonal $IgG_1$ antibody derived from said nonhuman source;

(f) a visualization reagent comprising peroxidase labeled polymer conjugated to affinity-isolated anti-said nonhuman source immunoglobulins;

(g) a substrate for said peroxidase labeled polymer;

(h) a chromogen comprising 3,3'-diaminobenzidine;

(i) Tris Buffered Saline, pH 7.6; and (j) a surfactant.

2. A kit operable for detecting the presence of epidermal growth factor receptor in cells comprising a tissue in accordance with claim 1 further comprising Tris-based antibody diluent comprised of 0.05M Tris-HCl pH 7.6 containing stabilizing protein and 0.015M sodium azide.

3. The kit operable for detecting the presence of epidermal growth factor receptor in cells comprising a tissue in accordance with claim 1 further comprising at least one control slide containing three pelleted, formalin-fixed, paraffin-embedded cell lines, which represent different amounts of the EGFR protein expression.

4. The kit operable for detecting the presence of epidermal growth factor receptor in cells comprising a tissue in accordance with claim 2 further comprising at least one control slide containing three pelleted, formalin-fixed, paraffin-embedded cell lines, which represent different amounts of EGFR protein expression.

5. The kit in accordance with claim 1 wherein said peroxidase block comprises 0.03% hydrogen peroxide containing sodium azide.

6. The kit in accordance with claim 2 wherein said peroxidase block comprises 0.03% hydrogen peroxide containing sodium azide.

7. The kit in accordance with claim 1 wherein said peroxidase block comprises 0.03% hydrogen peroxide containing sodium azide.

8. The kit in accordance with claim 3 wherein said peroxidase block comprises 0.03% hydrogen peroxide containing sodium azide.

9. The kit in accordance with claim 1 wherein said nonhuman source is a mouse.

10. The kit of claim 1 wherein said $IgG_1$ Isotype Control comprises monoclonal mouse $IgG_1$ antibody in concentrated form at 100 µg/mL as tissue culture supernatant (containing fetal calf serum) dialyzed against 0.05M Tris-HCl, pH 7.2, and 0.015M sodium azide.

11. The kit of claim 10 wherein said visualization reagent comprising peroxidase labeled polymer conjugated to affinity-isolated goat anti-mouse immunoglobulins in Tris-HCl buffer containing stabilizing protein and an antimicrobial agent.

12. The kit of claim 1 wherein said substrate includes a substrate buffer Buffer comprising Imidazole-HCl buffer pH 7.5, containing hydrogen peroxide, stabilizers, enhancers and an antimicrobial agent.

13. The kit of claim 1 wherein said surfactant is Tween 20.

* * * * *